(12) United States Patent
Duriseti et al.

(10) Patent No.: US 11,544,619 B2
(45) Date of Patent: Jan. 3, 2023

(54) DIMENSION REDUCTION OF CLAIMS DATA

(71) Applicant: BaseHealth, Inc., Sunnyvale, CA (US)

(72) Inventors: Amal Duriseti, Sunnyvale, CA (US); Li Lee, Sunnyvale, CA (US); Emin Martinian, Sunnyvale, CA (US)

(73) Assignee: BASEHEALTH, INC., Sunnyvale, CA (US)

( * ) Notice: Subject to any disclaimer, the term of this patent is extended or adjusted under 35 U.S.C. 154(b) by 992 days.

(21) Appl. No.: 16/237,954

(22) Filed: Jan. 2, 2019

(65) Prior Publication Data

US 2019/0205787 A1 Jul. 4, 2019

Related U.S. Application Data

(60) Provisional application No. 62/612,885, filed on Jan. 2, 2018.

(51) Int. Cl.
*G06N 20/00* (2019.01)
*G06F 17/16* (2006.01)
*G06F 16/901* (2019.01)
*G16H 10/00* (2018.01)
*G06F 16/906* (2019.01)
*G16H 50/20* (2018.01)
*G06Q 10/04* (2012.01)
*G16H 10/60* (2018.01)

(52) U.S. Cl.
CPC ........... *G06N 20/00* (2019.01); *G06F 16/901* (2019.01); *G06F 16/906* (2019.01); *G06F 17/16* (2013.01); *G06Q 10/04* (2013.01); *G16H 10/00* (2018.01); *G16H 10/60* (2018.01); *G16H 50/20* (2018.01)

(58) Field of Classification Search
CPC ..... G06N 20/00; G06F 16/901; G06F 16/906; G06F 17/16; G16H 10/00; G16H 10/60; G16H 50/20; G06Q 10/04
See application file for complete search history.

(56) References Cited

U.S. PATENT DOCUMENTS

2019/0096525 A1* 3/2019 Ferenc ............... G16H 50/70
2020/0134489 A1* 4/2020 Achin ................. G06Q 10/06

OTHER PUBLICATIONS

Gunasekar et al., "Phenotyping using Structured Collective Matrix, Factorization of Multi{source EHR Data", Sep. 14, 2016, arXiv: 1609.04466v1 [stat.AP], 19 Pages. (Year: 2016).*
Brown et al., "Machine Learning on Human Connectome Data from MRI", Nov. 26, 2016, Medical Image Analysis Lab, Simon Fraser University, Burnaby, BC, Canada, arXiv: 1611.08699v1 [cs.LG], 51 Pages. (Year: 2016).*

* cited by examiner

*Primary Examiner* — Gil H. Lee
*Assistant Examiner* — Chhian (Amy) Ling
(74) *Attorney, Agent, or Firm* — Dickinson Wright PLLC

(57) ABSTRACT

Various information systems may benefit from the appropriate simplification of data structures and processes. For example, certain health information systems may benefit from dimension reduction of claims data. A method can include creating a tensor to organize data. The method can also include conditionally reducing the size of that tensor in order to more effectively apply machine learning.

3 Claims, 2 Drawing Sheets

DIMENSION REDUCTION OF CLAIMS DATA

CROSS-REFERENCE TO RELATED APPLICATION

This application is a non-provisional of, and claims the benefit and priority of, U.S. Provisional Patent Application No. 62/612,885, filed Jan. 2, 2018, the entirety of which is hereby incorporated herein by reference.

BACKGROUND

Field

Various information systems may benefit from the appropriate simplification of data structures and processes. For example, certain health information systems may benefit from dimension reduction of claims data.

Related Art

Decision support tools, such as artificial intelligence and machine learning, may improve the health care system if they can be properly used. Currently, there are so many types of data available that it is hard for such tools to be trained effectively.

For example, one of the main types of data which is broadly collected for patients is claims data consisting of ICD-9 or ICD-10 claims codes. These are used to describe a diagnosis or procedure and the associated cost for the medical encounter. The national Medicare sample data on which much of the research on health analytics is conducted uses mainly this kind of data for analysis.

The difficulty with the raw claims data is that it is very large. The number of possible claims codes runs into the tens of thousands. In general, many machine learning tools have a complexity which goes up exponentially with the dimensions of the data. So categorical data with such large dimensions makes machine learning systems more time consuming to train as well as more likely to over-fit the data. As a result, most machine learning algorithms have significant difficulties in finding predictable patterns.

Simply using claims data by itself is sub-optimal. Ideally, one would like to also include data such as:
  i. Prescription drug information.
  ii. Vital statistics.
  iii. Patient risk factors.
  Such risk factors may include both medical measurements such as LDL, HDL, VLDL cholesterol levels, blood pressure, body mass index as well as behavioral risk factors such as diet, exercise, stress, amount of sleep, smoking, alcohol, and so on.
  iv. Demographic factors such as age, gender, socioeconomic status, and ethnicity.

While, in principle, having more data should enable better analysis, the sheer size, scale, and high dimensionality make it difficult to train machine learning systems effectively.

SUMMARY

Various embodiments relate to a method. The method can include creating a tensor to organize data. The method can also include conditionally reducing the size of that tensor in order to more effectively apply machine learning. Other embodiments relate to an apparatus configured to perform the method and a non-transitory computer-readable medium for performing the method when a stored program is executed.

BRIEF DESCRIPTION OF THE DRAWINGS

The drawings illustrate various embodiments by way of non-limiting examples.

DETAILED DESCRIPTION

Figure 1:
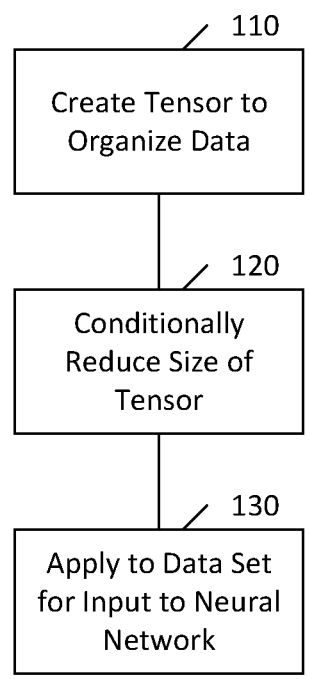
FIG. 1 illustrates a method according to certain embodiments.

Certain embodiments relate to a machine learning system to incorporate large amounts of data (including but not limited to claims data, diagnosis codes, procedure codes, prescriptions, vital statistics, as well as patient risk factors such as cholesterol levels, blood pressure, etc.) in order to model patient risk and suggest health interventions.

As noted above, the large amounts of health care data makes effectively training machine learning systems difficult. One goals of certain embodiments is to provide a system for preprocessing and organizing data to enable machine learning systems to more effectively incorporate large amounts of data. In addition to such preprocessing and data organization steps, certain embodiments relate to how these can be used in some example machine learning systems.

Certain embodiments provide a number of preprocessing approaches to reduce the dimensionality of raw claims data to more manageable levels. The preprocessed claims data can then be used as inputs to various machine learning algorithms.

Tensor Creation

We begin by describing a number of preprocessing or data organization methods. Some of these apply to claims data such as ICD-9 or ICD-10 data while others can apply to more general data such as generic patient risk factors. All of these examples start by creating a tensor to organize the data, then potentially reducing the size of that tensor in order to more effectively apply machine learning.

In this section we describe methods to collect data into tensors. A tensor is essentially a mathematical term for a multi-dimensional array of data similar to but more general than a matrix or vector. In mathematics, tensors should obey certain transformation laws but in machine learning and computer science these transformation laws are sometimes ignored and tensors are simply an abbreviation for "multi-dimensional array".

Raw claims data generally consists of many lines in a comma separated values (CSV) file. For example, this is how the national Medicare sample data is provided to researchers. As a first step we apply the following procedure to convert many lines of claims data into a more usable form.

We begin by creating a 4-dimensional tensor, T, initialized to all zeros with P rows, D date levels, C columns, and S "stacks" (which we discuss in more detail shortly). The parameter P is the number of patients in the data sample while C is the number of possible claims codes. For example, C will depend on whether ICD-9 or ICD-10 or some other coding format is used. The parameter D is the number of possible dates. For example, if we were to design T to include data for calendar year 2016 then D would correspond to 366 (since 2016 was a leap year). The parameter S is a system parameter chosen by the designer (e.g., S=20 would be a typical setting). We denote the element at row p, column c, date d and stack s as $T_{p,c,d,s}$ with indexes starting from 1 (i.e., $T_{1,1,1,1}$ is the lexicographically first element).

Each stack level essentially represents a type of data. This will depend on the data available in a health care system. As an example, one might consider a 20 level stack where the levels represent the following types of data as of the given date:
  i. Claim amount.
  ii. Patient gender.
  iii. Patient age in days.
  iv. Code for patient ethnicity.
  v. Code indicating health care provider.
  vi. Code for the region where the patient lives.
  vii. Systolic blood pressure.
  viii. Diastolic blood pressure.
  ix. Triglyceride level.
  x. LDL cholesterol level.
  xi. HDL cholesterol level.
  xii. VLDL cholesterol level.
  xiii. A1C level.
  xiv. Body mass index.
  xv. Most important diagnosis code.
  xvi. Most important procedure code.
  xvii. Second most important diagnosis code.
  xviii. Second most important procedure code.
  xix. Third most important diagnosis code.
  xx. Third most important procedure code.

Some of those entries may be redundant (e.g., patient gender may be redundant in the sense that it does not change throughout the patient records for most but not necessarily all patients). Others (e.g., LDL level) may represent the latest known reading if a reading is not available on the date for that entry. Still others may be null.

To populate the tensor, we may begin by going through the patient information as follows:
  i. When we encounter a claim for patient p date on date d for amount A, we may first determine the most important claim code for the encounter (call this code c). This may be the primary procedure code or something else.
  ii. Set stack level 1 for the corresponding cell to be the amount of the claim: $T_{p,c,d,1}=A$.
    We may use stack level 1 as the amount of the claim for illustrative purposes. In general, stack levels may corresponding to different values.
  iii. Set the remaining stack levels to the other information defined for the stack.
    For example, using the stack levels defined previously we would set $T_{p,c,d,2}$ to be the code for the patient gender, $T_{p,c,d,3}$ to be the patient's age in days, etc.

One benefit of organizing the data into the tensor T as described above is to transform a variety of disparate forms of data into a clear, well-defined, and relatively compact format. For example, claims data may come from one system a billing system while LDL cholesterol may come from a patient's electronic health record.

Tensor Date Summary

While the full tensor is a useful starting point, it will generally be too large to work with. The next step in our data organization method is to convert the full tensor T into a tensor date summary T' as follows:
  i. For each stack level, s, we may choose a summary function $G_s(\ )$ to collapse a vector into a scalar. For example, $G_s(\ )$ could correspond to summing, averaging, or concatenating elements.
  ii. For each stack level, s, we may choose a transform function, $F_s(\ )$. For example, $F_s(\ )$ could correspond to raising the input to a power, taking the logarithm of the input, applying a sigmoid function, and so on.
  iii. For patient p, date d and stack-level s, form the C-dimensional vector $W_c=G_s(T_{p,d,s})$, by applying the transform function to each element of T for that patient, date, and stack-level.
  iv. Summarize this vector by applying the summary function to obtain $F_s(W_c)$.
  v. Set the entry for (p, d, s) of the tensor date summary T' to be $T'_{p,d,s}=F_s(W_c)$.

The resulting tensor date summary T' is then a convenient summary of the full tensor with the date dimension removed. In our example where the 1st stack level is the claims amount, if $G_1$ corresponded to the sum and $F_1$ is the identity function $F_1(x)=x$, then the first stack level of T' would simply correspond to the sum of claims in the summary period. Similarly, if the 10th stack level is the LDL cholesterol reading, then if $G_{10}$ corresponded to the arithmetic average and $F_{10}$ is the identity function $F_{10}(x)=x$, then the tenth stack level of T' would correspond to the arithmetic average of LDL cholesterol readings over that set of dates.

As a slightly more advanced example, if stack level 9 in our example corresponds to the triglyceride level then we could choose $G_9$ as the sum and $F_9(x)=x^0$ to represent the count of triglyceride readings taken in the given period (with the understanding that a null reading would be ignored in the count). Sometimes we are interested in both the count and sum in which case we can use intermediate exponents such as $F_i(x)=|x|^{1/2}$.

One point here is that the procedure described above provides a useful way of collapsing a large tensor of patient data in some date window into a smaller tensor. These smaller tensors can then be used in machine learning algorithms or processed further as we describe later.

For example, imagine we wish to train a machine learning system to predict patient claims. One way we could do this is:
  i. Choose system parameters as discussed above.
  ii. Compute the full tensor using data in calendar year 2015. Denote this as T (2015).
  iii. Form the tensor date summary T' (2015).
  iv. Collect patient costs for calendar year 2016.
  v. Train a machine learning system (e.g., neural networks, support vector machines, linear or logistic regression, etc.) to predict the calendar year 2016 claims as a function of T' (2015).

In more advanced systems, it may be useful to have multiple tensor date summaries. For example, if we are training a system to predict 2016 patient claims using 2015 data, we could do the following:
  i. Choose system parameters as discussed above.
  ii. Compute 4 full tensor T(Q1),T(Q2),T(Q3),T(Q4) using data for each quarter in calendar year 2015.
  iii. Form a tensor date summary for each full tensor: T'(Q1),T'(Q2),T'(Q3),T'(Q4).
  iv. Collect patient costs for calendar year 2016.
  v. Train a machine learning system (e.g., neural networks, support vector machines, linear or logistic regression, etc.) to predict the calendar year 2016 claims as a function of T'(Q1),T' (Q2),T'(Q3),T'(Q4).

The above approach illustrates how we can concisely collect data into convenient tensor summaries while still maintaining some temporal sequence. This is useful as various neural networks can sometimes perform better with such structures.

Singular Value Decomposition (SVD)

The tensor date summary representation discussed previously is a convenient way to organize and summarize the raw data. Sometimes, however, even this is too much data for effective training of machine learning systems. Consequently, we now describe how to apply a singular value decomposition (SVD) to reduce the data size further.

The SVD is a linear algebra method used to find the most important components of a matrix. There are many ways to extract a matrix from the tensor date summary T'. One of the most natural is to take the level 1 stack denoted as $T'_{p,c,1}$. This is a matrix where the rows are patients, the columns are claims codes, and the entries are the summary of the claims amounts over the dates. For example, if $F_1(x)=x$ and $G_1( )$ is the sum, then $T'_{p,c,1}$ is a matrix where cell (p,c) is the total claims cost patient p incurred for claim c.

The matrix $T'_{p,c,1}$ is a concise summary of the claim costs since it holds the total cost for a patient over the period in question broken down by claims codes. A potential issue with this matrix, however, is that many claims codes may be similar. For example, there may be separate claims codes for paraplegia and quadriplegia but these are similar forms of paralysis. Many other such examples may exist. Similarly, there may be diseases which are different but tend to co-occur.

Essentially, one of our goals is to focus on a smaller set of "proto-claims" by grouping related claims codes together. This will allow us to convert the P-by-C matrix $T'_{p,c,1}$ into a smaller matrix with P rows but fewer columns corresponding to the proto-claims.

Using the SVD, we can decompose the matrix $T'_{p,c,1}$ into an equivalent matrix U Z V where Z is a diagonal and sorted so that the diagonal is in decreasing order and U and V are orthogonal. Note that $T'_{p,c,1}$=U Z V so we have not changed anything but simply written $T'_{p,c,1}$ in a more compact form. We can reduce the dimension of this matrix by truncating the U, Z, and V matrixes as follows. Define $U_L$ to be the matrix with only the first L column vectors of U, $Z_L$ to be the square diagonal matrix with only the largest L values of Z, and $V_L$ to be the matrix with only the first L row vectors of V. Then we can define the reduced dimension matrix $U_L Z_L V_L$ The matrix $U_L Z_L V_L$ is sometimes referred to as the "truncated SVD" which is the best reduced form version of the original matrix in a certain mathematical sense.

More generally, we can use the U and VL matrices to reduce the dimension of any P-by-C matrix A into a P-by-L matrix AL=$U^T$ A $V_L^T$ (where $U^T$ represents the transpose of the matrix U and $V_L^T$ represents the transpose of the matrix $V_L$). By applying this procedure to the claims matrix $T'_{p,c,1}$, we obtain the reduced form version T"=$U^T$ A $V_L^T$. This matrix T" is useful because it has replaced the original P-by-C matrix of patients and claims into a smaller P-by-L matrix of patients and "proto-claims".

One could apply the same procedure to reduce the size of the matrices at levels with s>1 or leave those levels unchanged depending on the specific details of the data. Finally one could train a machine learning system (e.g., neural networks, support vector machines, linear or logistic regression, etc.) using these reduced dimension matrices instead of the originals in a manner similar to what we described previously.

This provides a potentially large improvement in training since instead of dealing with C claims where C is often on the order of ten-thousand, we can choose L to be say 10 or 100.

CC Decomposition

The SVD decomposition described previously reduces the dimension of the data using a mathematical method of finding the important parts of the claims matrix. This is useful, but there are other ways to go about the task of dimension reduction which may take into account more information about how claims work.

We now describe such a method using the so-called Condition Codes (CCs) defined by the Center for Medicare and Medicaid Services (CMS). According to CMS, each ICD-9 or ICD-10 code can be mapped to a condition code which collects together more specific conditions such as paraplegia and quadriplegia into a more general category such as paralysis. Let us denote the condition code for claim code x and CC(x).

Using the condition codes, we can then reduce the claims matrix $T'_{p,c,1}$ discussed in the Tensor Date Summary section as follows.

i. Set the reduced dimension matrix $T_{p,c,1}$ to be a matrix with P zeros and L columns where L is the number of possible condition codes (generally this is on the order of a hundred).

ii. For each patient p and condition code cc, form the list of all entries $T'_{p,c,1}$ such that CC(c)=cc. Said another way, we are finding a list of all the claims codes c which map to the condition code cc.

iii. Summarize this list using a summary function. For example, it may be reasonable to apply whichever summary function was used for the stack level 1 summary, $G_1( )$ discussed earlier although in principle other summary functions could be used as well.

iv. Place the result from the previous step into $T''_{p,c,1}$.

For example, if we used the simple sum as the summary function in step 3, the net effect would be to form each entry of $T''_{p,c,1}$ by summing all the claims in T' for patient p which map to condition code cc. In the case where cc corresponds to the condition code for paralysis, this would be like summing all the individual claims related to paraplegia, quadriplegia, and so on into a single entry.

This same approach could be applied to other stack levels of T' besides just the claims matrix or it could be applied only to the claims matrix. Machine-learning techniques could then be used on the reduced dimension matrices as described previously.

Generalized Claim Code Mappings

Of course, one does not have to use the condition codes defined by CMS. One could use any other more general grouping of ICD codes into broader categories. The basic concept is that one may like to group together conditions which may be related or tend to occur together in patients.

There are many ways to do this. Before going into some specific examples, we find it useful to define the concept of a generalized claim code mapping. Consider a dataset with C possible values for the claim code and define an L dimensional generalized claim code mapping (L-GCCM) as a function which maps the claim code c into the L dimensional real valued vector: WV(c). Each element of WV(c) can be considered a proto-claim as we describe shortly.

Once we have trained an L-GCCM (in a manner we describe later), it can be applied to a matrix of patients and claims such as the matrix $T'_{p,c,1}$ we have discussed earlier as follows:

i. Define a set of C scalar transformation functions $F_c(m_c)$ where for simpler notation we denote the cost in column c as $m_c=T'_{p,c,1}$.

$F_c( )$ may be used to transform the claim cost for claim c.

Often one can just use the same function for each c, but for certain claims one may want to use something different so we describe the general case.

Reasonable examples include a simple linear function $F_c(x)=x$, a count function such as $F_c(x)=0$ if x is 0 otherwise 1, or a power function which lies somewhere between them such as $F_c(x)=|x|^{1/2}$.

ii. For patient p, define row p of the reduced form matrix $T''_{p,1}$ as $T''_{p,1}=G[WV(1) F_1(m_1), WV(2) F_2(m_2), \ldots, WV(C) F_C(m_C)]$ where G( ) is a summary function similar to the ones described earlier to combine claims columns.

Said another way, we may represent the claims for patient p as the weighted combination of the vectors WV(C) for each claim the patient has where the weights are the scalar transformations of the claims and the "combination" is according to the summary function G ( ).

For example, if G ( ) is the sum function, then row p of the resulting matrix is the weighted sum of the proto-claim vectors: $T''_{p,1}=\Sigma_C G[WV(c) F_c(m_c)]$.

To summarize, some ideas which may make the L-GCCM useful are:
i. Mapping each of the C possible claims for a patient to an L-dimensional proto-claim vector WV(c).
ii. Weighting the proto-claim vector by some function of claims cost for a patient.
iii. Combining the weighted proto-claim vectors.
iv. Replacing row p of $T''_{p,c,1}$ with the combined, weighted proto-claim vectors to get an L-dimensional version of the original C-dimensional row.

Example 2-GCCM

Let us consider an example to illustrate this process. For simplicity, imagine that there are only 3 possible claims codes from ICD-10:
Code 1: G041=Tropical spastic paraplegia
Code 2: G723=Periodic paralysis
Code 3: I281=Aneurysm of pulmonary artery Furthermore imagine that we have 2-GCCM which maps a general claim code into a two-dimensional vector. If this is a good GCCM, then we would expect WV(1) to be similar to WV(2) since both are forms of paralysis. We would also except WV(3) to be different from both. For example, imagine that these codes are mapped to the following vectors:
G041→(0.96, 0.28)
G723→(1, 0)→(1.0)
I281→(0, 1)

Next, consider a claims matrix with the following contents:
The first row is (1500,0,100) corresponding to a patient who has claims for paraplegia and small claim for heart related problems (e.g., perhaps a check-up from a previous episode).
The second row is (0,2000,0) corresponding to a patient with periodic paralysis.
The third row is (0,0,5000) corresponding to a patient with a claim for heart disease (perhaps for treatment of an aneurysm).

The process we describe would compute the reduced form matrix T" as:
The first row would be 1500 WV(1)+100 WV(3). This adds the proto-claim vector for paraplegia weighted by the amount of the paraplegia claim to the proto-claim vector for cardiac problems weighted by the claim amount.
The second row would be 2000 WV(2). This is the periodic paralysis proto-claim vector weighted by the amount of the claim.
The third row would be 500 WV (3).

Using the L-GCCM

A benefit of the L-GCCM is that we have reduced a claims matrix with P rows and C columns into a claims matrix with P rows and L columns. In the initial version, the C columns corresponded to the amount of claims (or number of claims or some other function of claims depending on the transformation function used) for each single possible claim code. In ICD-10, there would be many thousands of possible claims codes. In the L-GCCM, each claim code was mapped to an L-dimensional vector which were then combined using a summary function.

One of the ideas here is that we may start with claims codes such as G041 and G723 that cannot be easily combined and turn them into vectors such as (0.96, 0.28) and (1,0) so that we can then combine them. This is a generalization of the CC decomposition described earlier in that we may use the GCCM function to map each claim to its own WV vector and then combine the WV vectors. This procedure can also be used on other stack levels of the tensor.

Finally, the reduced form tensor can be used as input to further machine learning algorithms which may tend to be effective because the data size is smaller.

Using Word2Vec for Claims GCCM

One way to create a generalized decomposition is to use the well-known "Word2Vec" algorithm. Word2Vec was originally developed in the context of natural language processing (NLP). The motivation was that training machine learning algorithms against a large vocabulary is difficult. The Word2Vec algorithm was designed to reduce the dimension of the vocabulary by clustering words together.

In embodiments of our application, we may use the Word2Vec algorithm in a novel way by considering claims codes as analogous to "words" and patient claim histories as analogous to "documents". We first describe how to map a patient's claims history into a "document".

i. Initialize an empty list called the "output list" which may be updated in the following steps and represent the final output when finished.
ii. Step through the claims for the patient and do the following for each claim.
iii. Order the diagnosis codes and procedure codes from most important to least important (or vice versa). For example, a reasonable approach would be to start with the primary diagnosis code, then the primary procedure code, then the secondary diagnosis code, then the secondary procedure code, and so on.
iv. Extend the output list with the ordered list of diagnosis codes from the previous step.

An example may be helpful. Imagine we have a patient with three claims in the period of interest. Imagine the first claim has diagnosis codes (A, B, C) and procedure codes (D, E, F) while the second claim has diagnosis codes (U, V, W) and procedure codes (X, Y, Z). The output of the above process would be (A, D, B, E, C, F, U, X, V, Y, W, Z).

We may do the above for each of the P patients in our dataset to obtain P documents. We may then choose the parameters for the Word2Vec algorithm (e.g., the context size N and a dimension size Z). We may then feed these documents into the Word2Vec algorithm (e.g., as implemented in the genism python software package) to obtain the trained model. Finally, we may apply the trained model to map each claims code to a vector and then combine them as described previously.

For many of these generalized decompositions but for Word2Vec in particular, it may be worth noting that the initial WV vectors may often not be normalized. That is, they may have significantly different magnitudes so that the norm of WV(1) is quite different than the norm of WV(2). In such cases, it may often be helpful to normalize the WV vectors so that each has unit norm before combining. Also, in such cases it may sometimes be useful to use a summary function, G( ) which is the average instead of the sum in order to account for the fact that patients may have differing numbers of claims.

Other Embedding Techniques

While we have described using SVD and Word2Vec in detail, other embedding techniques may also work. This general insight is part of the reason why we outlined the context of an L-GCCM separately from something like Word2Vec. In the interest of clarity, at least two other word embedding methods that can be used included the Fasttext algorithm published by Facebook and the Glove algorithm from Stanford.

Multi-Stage Combinations

The techniques above can also be applied in multiple stages depending on the application, data availability, and so on. For example, one could first apply the CC Decomposition described previously to map claims codes to the CMS condition codes. This would reduce the dimension of the patient/claims matrix from having thousands of columns to hundreds of columns.

Then one could apply a technique from Generalized Claim Code Mapping such as Word2Vec to further map the condition code representation into a smaller space. This would reduce the dimension of the patient/claims matrix from hundreds of columns to say 30 columns.

Generalized Clustering

The previous sections on the Singular Value Decomposition, CC Decomposition, and Generalized Claim Code Mappings provided dimension reduction by first mapping individual claim codes into vectors and then combining the vectors. A goal is essentially to take a very large dimensional space of patients and claims data and cluster them into a smaller space for easier processing.

Another way to accomplish this same goal is to do the clustering jointly instead of first mapping claims codes to vectors and then combining the vectors.

Generalized Clustering with Doc2Vec

One way to do this joint clustering is to use the doc2vec algorithm (e.g., as implemented by the gensim software package for the python programming language). Going into the full details of doc2vec is beyond the scope of this work. Roughly speaking, however, doc2vec works by taking "documents" of "words" and mapping them into vectors. We can use doc2vec in embodiments of our application by considering a patient to be a "document" and the "words" to be the claims codes.

In detail, this may work as follows:
i. For each patient, p, initialize an empty list called the "output list" which may be updated in the following steps.
ii. Step through the claims for the patient and do the following for each claim.
iii. Order the diagnosis codes and procedure codes from most important to least important (or vice versa). For example, a reasonable approach would be to start with the primary diagnosis code, then the primary procedure code, then the secondary diagnosis code, then the secondary procedure code, and so on.
iv. Extend the output list with the ordered list of diagnosis codes from the previous step.
v. Pass the list to the doc2vec algorithm as an input "document" with document tag p.
vi. Run the doc2vec algorithm.

The output of the doc2vec algorithm is a set of document vectors representing the patients. In our notation, the rows of T" are then these p document vectors representing the patients. Effectively, the doc2vec algorithm may take in an arbitrary number of claims codes for each patient and map these directly to a vector so that patients with similar claims end up with similar vectors. Machine learning can then be conducted on these patient vectors more efficiently.

Further Machine Learning

Once one has obtained either the date summary tensor T' or one of the reduced form T" versions discussed above, a variety of machine learning techniques can be applied. This may include linear regression, random forests, neural networks, and so on.

One potential natural goal for the machine learning algorithm may be to predict the total claims for year t+1 from claims data from year t. Another approach may be to predict which patients are likely to be in the highest cost decile, quintile, etc., in year t+1 based on claims data in year t.

In this process, one can either use the preprocessed data as is and train the parameters of the machine learning algorithm (e.g., the regression coefficients in a linear regression) or also allow the machine learning algorithm to affect the form of the dimensionality reduction (e.g., the exponent p in a transform function of the form $T(x)=|x|^p$).

FIG. 1 illustrates a method according to certain embodiments. As shown in FIG. 1, a method can include, at 110, creating a tensor to organize data. The method can also include, at 120, conditionally reducing the size of that tensor in order to more effectively apply machine learning. The method can further include, at 130, applying the reduction in size of the tensor to a data set for input to a neural net. These steps can be carried out according to any of the examples described above, in any of their variants and in any combination.

Figure 2:
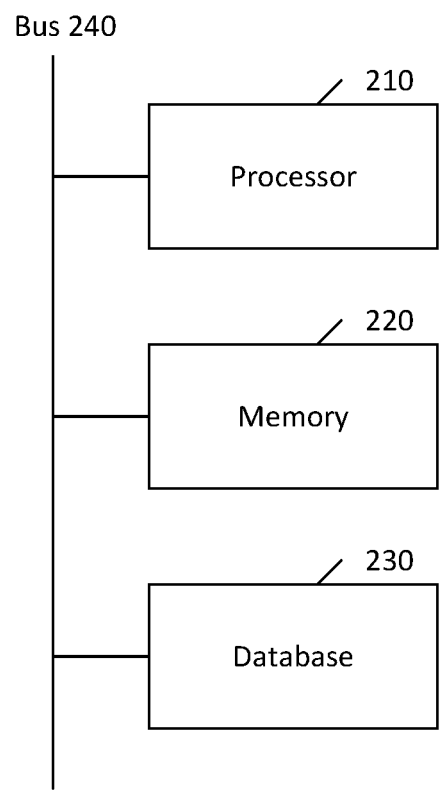
FIG. 2 illustrates a system according to certain embodiments.

The above method can be variously implemented, for example by computer system(s). FIG. 2 illustrates an example system that can implement the above-described methods in any of their variations.

As shown in FIG. 2, a system can include at least one processor 210 and at least one memory 220 including computer program instructions. The processor 210 and the memory 220 can be implemented separately or together. For example, the processor 210 and the memory 220 can be implemented on a same chip or on different computing systems.

The processor 210 can be any computational engine, such as any controller or central processing unit (CPU), having one processing core or multiple processing cores. The processor 210 may be a microprocessor, an application specific integrated circuit, or a field programmable gate array. Other implementations are also permitted.

The memory 220 can be any readable memory, such as a non-transitory computer-readable medium. The memory 220 can be any form of storage, such a optical storage, magnetic storage, or any form of random access memory (RAM) or read only memory (ROM).

The system can also include one or more database 230. The database 230 may be embodied in computer-readable medium, such as a storage array or hard disk drive. Other embodiments are also permitted.

The system can further include one or more bus 240, or other interconnection hardware. For example, the system can include one or more network interface cards, modems, or the like. The system is shown as though the bus 240 directly connects the processor 210, memory 220, and database 230, but other implementations are permitted. For example, the database 230 may be remote.

The at least one memory 220 and the computer program instructions can be configured to, with the at least one processor 210, cause the system at least to perform the above-described methods in any of their variations. The system can access database 230 to obtain various health information.

What is claimed is:

1. A system comprising:
at least one processor and at least one memory including computer program code, wherein the at least one memory and the computer program code are configured to, with the at least one processor, cause the system to execute steps including:
creating a 4-dimensional tensor T to organize data, the tensor T, having dimensions regarding P patient rows, D date levels, C claim code columns encoding medical diagnosis and/or procedure coding data regarding a patient identified by index P, and S stacks regarding data types, and initializing each value thereof to zero;
populating the tensor T with patient data, date data, coding data, and data type information;
converting the full tensor T into a tensor date summary T'; and
conditionally reducing the size of tensor date summary T' in order to more effectively apply machine learning, further comprising the steps of:
mapping each of one or more C possible claims for a patient to an L-dimensional proto-claim vector WV(c);
weighting each of the proto-claim vectors WV(c) by a function of claims cost for the patient;
combining the weighted proto-claim vectors; and
replacing row p of $T'_{p,c,1}$ with the combined, weighted proto-claim vectors to get an L-dimensional version of the original C-dimensional row.

2. An apparatus, comprising:
at least one processor; and
at least one memory including computer program code, wherein the at least one memory and the computer program code are configured to, with the at least one processor, cause the apparatus at least to:
create a 4-dimensional tensor T to organize data, the tensor T, having dimensions regarding P patient rows, D date levels, C claim code columns encoding medical diagnosis and/or procedure coding data regarding a patient identified by index P, and S stacks regarding data types, and initializing each value thereof to zero;
populate the tensor T with patient data, date data, coding data, and data type information;
convert the full tensor T into a tensor date summary T'; and
conditionally reduce the size of tensor date summary T' in order to more effectively apply machine learning, further comprising the steps of:
mapping each of one or more C possible claims for a patient to an L-dimensional proto-claim vector WV(c);
weighting each of the proto-claim vectors WV(c) by a function of claims cost for the patient;
combining the weighted proto-claim vectors; and
replacing row p of $T'_{p,c,1}$ with the combined, weighted proto-claim vectors to get an L-dimensional version of the original C-dimensional row.

3. A non-transitory computer-readable medium encoded with instructions that, when executed in hardware, perform a process, the process comprising:
creating a 4-dimensional tensor T to organize data, the tensor T, having dimensions regarding P patient rows, D date levels, C claim code columns encoding medical diagnosis and/or procedure coding data regarding a patient identified by index P, and S stacks regarding data types, and initializing each value thereof to zero;
populating the tensor T with patient data, date data, coding data, and data type information;
converting the full tensor T into a tensor date summary T'; and
conditionally reducing the size of tensor date summary T' in order to more effectively apply machine learning, further comprising the steps of:
mapping each of one or more C possible claims for a patient to an L-dimensional proto-claim vector WV(c);
weighting each of the proto-claim vectors WV(c) by a function of claims cost for the patient;
combining the weighted proto-claim vectors; and
replacing row p of $T'_{p,c,1}$ with the combined, weighted proto-claim vectors to get an L-dimensional version of the original C-dimensional row.

* * * * *